United States Patent [19]

Beppu et al.

[11] Patent Number: 4,690,918

[45] Date of Patent: Sep. 1, 1987

[54] USE OF TRICHOSTATIN COMPOUNDS FOR TREATING TUMOR CELLS

[75] Inventors: Teruhiko Beppu, 1-5-21, Horinouchi, Suginami-ku, Tokyo; Yasushi Iwamoto, Okegawa; Minoru Yoshida, Tokyo, all of Japan

[73] Assignee: Teruhiko Beppu, Tokyo, Japan

[21] Appl. No.: 821,973

[22] Filed: Jan. 24, 1986

[30] Foreign Application Priority Data

Jan. 30, 1985 [JP] Japan .................. 60-16085

[51] Int. Cl.⁴ .............................. A61K 31/70
[52] U.S. Cl. .................... 514/23; 536/17.2; 536/22; 536/18.7
[58] Field of Search ............ 536/22, 17.2, 18.7; 514/23

[56] References Cited

U.S. PATENT DOCUMENTS 4,218,478  8/1980  Omura et al. ................. 424/324

OTHER PUBLICATIONS

Yoshida et al., "Chem. Abst.", vol. 102, 1985, P. 199, 257 (s).
Morioka et al., "Chem. Abst.", vol. 104, 1985, p. 4632 (w).
Tsuji et al., "A New Antifungal Antibiotic, Trichostatin", *J. of Antibiotics*, vol. XXIX, No. 1, Jan. 1976, pp. 1-6.
Tsuji et al., "Trichostatin C, A Glucopyranosyl Hydroxamate", *J. of Antibiotics*, vol. XXXI, No. 10, Oct. 1978, pp. 939-944.
Fleming et al., "The Total Synthesis of (+)-Trichostatin A", *Tetrahedron*, vol. 39, No. 6, 1983, pp. 841-846.

*Primary Examiner*—Johnnie R. Brown
*Attorney, Agent, or Firm*—Oblon, Fisher, Spivak, McClelland, & Maier

[57] ABSTRACT

A method for inducing the differentiation of tumor cells in human or animal, which comprises administering an effective amount of trichostatin A and/or trichostatin C to the human or animal.

4 Claims, No Drawings

USE OF TRICHOSTATIN COMPOUNDS FOR TREATING TUMOR CELLS

The present invention relates to an antitumor drug. More particularly, the present invention relates to a novel use of a compound of the formula:

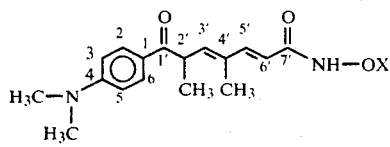

wherein X is a hydrogen atom or a group of the formula:

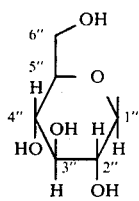

as an antitumor drug which inhibits proliferation of tumor cells in human or animal by inducing the differentiation of the tumor cells.

Tumors are generally classified into solid tumors and liquid tumors (hematopoietic organs). Treatments of tumors are generally classified into surgical therapy, drug therapy and radiation therapy.

For the treatment of a solid tumor such as gastric cancer, surgical therapy or a combination of surgical therapy and radiation therapy has been traditionally employed as the first choice. Once the metastasis is observed, drug therapy is used as a secondary or tertiary method of treatment. On the other hand, in the case of a liquid tumor such as leukemia, drug therapy is applied immediately after the positive diagnosis.

Tumours are not a single type of diseases and show different sensitivities to various therapeutic methods. As mentioned above, however, the significance of drug therapy is extremely great in any type of tumors.

Such drug therapy includes chemotherapy, immunotherapy and hormonetherapy. Among them, the most important therapy at present is chemotherapy which inhibits the metabolism of tumor cells by a direct action to tumor cells, or which inhibits proliferation of tumor cells by suppressing the DNA synthesis.

At least some tumor cells are considered to be undifferentiated cells wherein the differentiation is interrupted for some reasons. Heretofore, some studies have been made to differentiate such tumor cells to convert the undifferentiated cells to functional cells i.e. terminal cells. In general, terminal cells do not proliferate, and therefore a drug which is capable of inducing the differentiation of tumor cells, can be an effective antitumor agent. For instance, there have been known some substances which are capable of inducing the differentiation of Friend leukemia cells as one type of experimental models. For instance, low molecular polar compounds such as dimethylsulfoxide (DMSO) and hexamethylenebisacetamide (HMBA) which are believed to act on the cell membranes of tumor cells to exhibit their effectiveness, have strong activities for inducing the differentiation. However, such activities are obtainable only at a high concentration of from some mM to some hundreds mM (Proceedings of the National Academy of Sciences of the U.S.A., vol. 73, No. 3, p 862-866, 1976, published by the National Academy of Sciences of the United States of America). Therefore, it is difficult to use them for practical applications. On the other hand, some carcinostatic antibiotic substances such as bleomycin and mitomycin C which are believed to act on DNA, have been reported to have activities for inducing the differentiation of tumor cells at low concentrations. However, such activities are generally weak (Cancer Research, vol. 38, p 841-849, 1978, published by the Official Organ of the American Association for Cancer Research, Inc.). In the case of Friend leukemia cells, there is a general tendency (although there are some variations depending upon the particular cell strains used) that substances acting on the cell membranes require high concentration although their differentiation-inducing activities are strong, and substances acting on DNA are weak in their activities although they show the activities at a low concentration.

Under the circumstances, it has been strongly desired to develop an antitumor drug which has high carcinostatic activities and which has high selective toxicity against tumor cells.

Accordingly, it is an object of the present invention to provide an antitumor drug which not only exhibits strong carcinostatic activities at a low concentration but also exhibits extremely high selective toxicity to cancer cells, i.e. an extremely strong and highly safe antitumor drug.

The present invention is based on a discovery that the compounds of the above-mentioned formula I have such excellent antitumor activities.

The compounds of the formula I are known compounds. Namely, the compound wherein X is a hydrogen atom is trichostatin A (the Journal of Antibiotics, vol. 29, No. 1, p 1-6, 1976, published by Japan Antibiotics Research Association), and the compound wherein X is the group of the formula II is trichostatin C (the Journal of Antibiotics, vol. 31, No. 10, p 939-944, 1978). Both compounds have been known to have antifungal activities, but their antitumor activities have not been known.

Thus, the present invention provides a method for inducing the differentiation of tumor cells in human or animal, which comprises administering an effective amount of trichostatin A and/or trichostatin C to the human or animal.

Now, the present invention will be described in detail with reference to the preferred embodiments.

The compounds of the present invention may be in the form of pharmaceutically acceptable salts. As such pharmaceutically acceptable salts, any salts may be used so long as they do not adversely affect the desired pharmacological effects of the compounds. The selection and the production thereof can readily be made by those skilled in the art. For instance, as a pharmaceutically acceptable salt, an alkali metal salt such as a sodium salt or a potassium salt, an alkaline earth metal salt such as a calcium salt or a magnesium salt, a salt with an organic base such as an ammonium salt, or a salt with an organic base such as a triethylamine salt or an ethanolamine salt, may be employed.

The carcinostatic activities of the antitumor drugs of the present invention were determined by using Friend leukemia cells (see Test Example 1 given hereinafter).

Friend leukemia cells are cells which are commonly used as one of experimental cancer models for the researches on the inducement of the differentiation of tumour cells (Annual Review of Biochemistry, vol. 47, p 419–448, 1978, published by Annual Review Inc., U.S.A.). They are tumor cells of a mouse, which proliferate with the differentiation of the proerythroblasts being suspended by the infection with Friend virus. These tumor cells are undifferentiated proerythroblast cells, and therefore do not produce hemoglobin. However, once they are differentiated to red blood cells, such cells produce hemoglobin. Therefore, the degree of differentiation can be evaluated on the basis of the hemoglobin production.

Various substances have been known as substances for inducing the differentiation of tumor cells. For instance, the above-mentionied dimethylsulfoxide (DMSO) and hexamethylenebisacetamide (HMBA) may be mentioned.

The fact that the antitumor drugs of the present invention exhibit strong activities for inducing the differentiation of tumor cells at an extremely low concentration, was confirmed also with respect to erythroleukemia cells derived from a mouse like Friend leukemia cells, formed by the infection with Rausher virus (see Test Example 2 given hereinafter). As a substance of which the activities for inducing the differentiation has been confirmed by such erythroleukemia cells, 12-O-tetradecanoylphorbol-13-acetate (TPA), dimethylsulfoxide (DMSO) of hexamethylenebis-acetamide (HMBA) has been known.

The fact that the antitumor drugs of the present invention have extremely high selective toxicity against tumor cells, has been confirmed by comparing the activities against the tumour cells formed by the infection with tumor virus SV 40 and against the normal parent cells (see Test Example 3 given hereinafter).

The antitumor drugs of the present invention may be administered orally or non-orally. In the case of oral administration, they may be administered in the form of soft and hard capsules, tablets, granules, powders or the like. In the case of non-oral administration, they may be administered in the form of injection solutions, drip infusion formulations, or formulations such as suppositories whereby continuous membrane absorption can be maintained in the form of solid or viscous liquid of suspension. The selection of the method of preparation of these formulations and the vehicles, disintegrators or suspending agents, can readily be made by those skilled in the art. The antitumor drugs of the present invention may contain a further substance having carcinostatic activities, in addition to the compounds of the formula I or their pharmaceutically acceptable salts.

The amount of the active ingredients in the antitumor composition of the present invention may vary depending upon the formulation, but is usually from 0.1 to 50% by weight irrespective of the manner of administration.

The dose is determined taking into consideration the age, sex and symptom of disease of the patient, the desired therapeutic effect, the period for administration, etc. However, preferably a daily dose of the active ingredient is from 0.05 to 100 mg for an adult.

Now, the present invention will be described in further detail with reference to Examples and Test Examples. However. it should be understood that the present invention is by no means restricted by these specific Examples.

EXAMPLE (Formulation Example)

5 mg of trichostatin A as an active ingredient of the antitumor drug of the present invention, was dissolved in a mixture comprising 1 g of purified sesame oil and 100 mg of aluminum stearate gel. The solution thus obtained was introduced in an amount of 0.5 ml each into capsules to obtain capsules for oral administration.

TEST EXAMPLE 1

(Differentiation-inducing effects on Friend leukemia cells)

(1) Test Method

Culture medium used: 9.4 g of Eagle MEM No. 1 culture medium (manufactured by Nissui Seiyaku K.K.), 0.3 g of L-glutamine and 2 g of sodium bicarbonate were dissolved in 1 liter of distilled water, and then fetal calf serum (manufactured by Armour Pharmaceutical Co.) was added in an amount such that the final concentration would be 12% by volume.

Into a cluster dish with 24 perforations made of Coster Co., U.S.A., 0.5 ml of the above culture medium, $1 \times 10^5$ cells/ml of Friend leukemia cells DS 19 strain (obtained from the Institute of Applied Microbiology of Tokyo University) and the test compound in a concentration as identified in Table 1, were introduced, and the cells were cultured in a 5% carbon dioxide gas incubator at 37° C. Five days later, the cells were collected by centrifugal separation, and dyed with benzidine. The cells which underwent differentiation and became red blood cells, produce hemoglobin, and they can be counted under microscopic observation by using a hemocytometer in accordance with the Orkin's benzidine dyeing method. The ratio of the number of benzidine positive cells to the total number of cells thus counted was obtained as the differentiation-inducing rate.

$$\text{Differentiation-inducing rate (\%)} = \frac{\text{Number of benzidine positive cells}}{\text{Total number of cells}} \times 100$$

(2) Test results

TABLE 1

| Trichostatin A | | Trichostatin C | |
| --- | --- | --- | --- |
| Concentration (μg/ml) | Differentiation-inducing rate (%) | Concentration (μg/ml) | Differentiation-inducing rate (%) |
| 0 (control) | <1 | 0 (control) | <1 |
| 0.002 | 6 | 0.1 | 12 |
| 0.003 | 34 | 0.2 | 53 |
| 0.004 (0.013 μM) | 72 | 0.3 (0.65 μM) | 79 |

Hexamethylenebisacetamide (HMBA) which has been known to exhibit the strongest differentiation-inducing activities against Friend leukemia cells DS 19 strain, was tested at the same time, whereby the differentiation-inducing rate was 75% at a concentration of 4 mM. As calculated from the data shown in Table 1, the amount required to obtain the same differentiation-inducing rate, is about 1/310,000 (as calculated from 0.013 μM) in the case of trichostatin A. or about 1/6.200 (as calculated from 0.65 μM) in the case of trichostatin C. Thus, the antitumor drugs of the present invention have remarkably superior activities for inducing the differentiation of tumor cells.

TEST EXAMPLE 2

(Differentiation-inducing effects on Rausher virus infected leukemia cells)

(1) Test method

Culture medium used: 10.2 g of RPM I 1640 No. 2 culture medium (manufactured by Nissui Seiyaku K.K.), 0.3 g of L-glutamine and 2 g of sodium bicarbonate were dissolved in 1 liter of distilled water, and then fetal calf serum (manufactured by Armour Pharmaceutical Co., U.S.A.) was added in an amount such that the final concentration would be 12% by volume.

In the same manner as in Test Example 1, the differentiation-inducing rate against erythroleukemia cells RV-133 derived from a mouse (obtained from Institute of Applied Microbiology of Tokyo University) was measured.

(2) Test results

TABLE 2

| Trichostatin A | | Trichostatin C | |
|---|---|---|---|
| Concentration (μg/ml) | Differentiation-inducing rate (%) | Concentration (μg/ml) | Differentiation-inducing rate (%) |
| 0 (control) | <5 | 0 (control) | <5 |
| 0.004 | 32 | 0.1 | 62 |
| 0.005 | 52 | 0.2 | 85 |
| 0.006 | 67 | 0.3 | 92 |

The above data indicate that the active ingredients of the antitumor drugs of the present invention exhibit strong differentiation-inducing activities at an extremely low concentration at a level of less than 1 mg/ml also against erythroleukemia cells formed by the infection with Rauscher virus, as in the case against Friend leukemia cells.

TEST EXAMPLE 3

(Selective toxicity against tumor cells)

Toxicity of the active ingredients of the antitumor drugs of the present invention was compared as between against normal fibroblast cells taken from the kidney of a C3H/He mouse (C3H-2K) (obtained from the Institute of Medical Science of Tokyo University) and against tumor cells formed by the infection of the same cells with tumor virus SV40 (SV40-C3H-2K) (obtained from the same Institute).

(1) Test method

Culture medium used: same as used in Test Example 1

Into cluster dish with 24 perforations made by Costar Co., U.S.A., 0.9 ml of the above culture medium and 0.1 ml of a cell suspension prepared to contain $1 \times 10^6$ cells/ml were introduced to bring the cell density to a level of $1 \times 10^5$ cells/ml. The cells were cultured in a 5% carbon dioxide gas incubator at 37° C. overnight. Then, after replacing the culture medium with a fresh medium, a methanol solution of the test compound was added in the concentration as identified in Table 3, and the culturing was continued. Upon expiration of 72 hours from the addition of the test compound, the culture medium was removed, and the deposited cells were suspended by trypsin treatment. The dead cells were dyed by a trypan blue dyeing method, and the number of survived cells were counted on a red hemocytometer. The cell-growth inhibiting rate (%) calculated by the following formula was used as a reference for the evaluation of the selective toxicity.

$$\text{Growth inhibiting rate (\%)} = \left(1 - \frac{\text{Number of survived cells in each test group}}{\text{Number of survived cells in the control group}}\right) \times 100$$

(2) Test results

TABLE 3

| Concentration (μg/ml) | Growth inhibiting rate of C3H-2K (%) | Growth of inhibiting rate of SV40-C3H-2K (%) |
|---|---|---|
| | Trichostatin A | |
| 0.001 | 6.5 | 45 |
| 0.005 | 52 | 80 |
| 0.02 | 52 | 97 |
| | Trichostatin C | |
| 0.02 | 21 | 36 |
| 0.1 | 26 | 76 |
| 1 | 49 | 94 |

From the above data, it is evident that the difference in the toxicity of the active ingredients of the antitumor drugs of the present invention against the normal cells and against the tumor cells is extremely large, and thus proves that the active ingredients have remarkably high selective toxicity against the tumor cells.

As described in the foregoing, the present invention provides antitumor drugs which not only exhibit strong carcinostatic activities at an extremely low concentration but also have extremely high selective toxicity against tumor cells, i.e. extremely strong and highly safe antitumor agents.

What is claimed is:

1. A method for inducing the differentiation of tumor cells, which comprises administering an effective amount of trichostatin A, trichostatin C, or a mixture of trichostatin A and trichostatin C to a recipient.

2. The method according to claim 1, wherein the effective amount of trichostatin A, trichostatin C, or a mixture of trichostatin A and trichostatin C is administered in combination with a pharmaceutically acceptable carrier.

3. A method for inhibiting proliferation of tumor cells, which comprises administering a therapeutically effective amount of trichostatin A, trichostatin C, or a mixture of trichostatin A and trichostatin C to a recipient.

4. A method for inhibiting proliferation of tumor cells, which comprises inducing the differentiation of the tumor cells by administering an effective amount of trichostatin A, trichostatin C, or a mixture of trichostatin A and trichostatin C to a recipient.

* * * * *